United States Patent [19]

Digby et al.

[11] 4,169,480

[45] Oct. 2, 1979

[54] DEMAND PACER WITH PROGRAMMABLE RATE HYSTERESIS

[75] Inventors: Dennis Digby, Brooklyn Park, Minn.; John W. Keller, Jr., Miami, Fla.

[73] Assignee: Biotronik Mess- und Therapiegerate GmbH & Co., Berlin, Fed. Rep. of Germany

[21] Appl. No.: 917,141

[22] Filed: Jun. 19, 1978

[30] Foreign Application Priority Data

Aug. 19, 1977 [GB] United Kingdom ............... 34913/77

[51] Int. Cl.² ............................................. A61N 1/36
[52] U.S. Cl. ............................................. 128/419 PG
[58] Field of Search ................................. 128/419 PG

[56] References Cited

U.S. PATENT DOCUMENTS

| | | | |
|---|---|---|---|
| 3,623,486 | 11/1971 | Berkovits | 128/419 PG |
| 3,661,157 | 5/1972 | Fyson et al. | 128/419 PG |
| 3,717,153 | 2/1973 | Bowers | 128/419 PG |
| 3,794,045 | 2/1974 | Thaler | 128/419 PG |
| 3,833,005 | 9/1974 | Wingrove | 128/419 PG |
| 3,945,387 | 3/1976 | Adams | 128/419 PG |
| 3,972,334 | 8/1976 | Wickham | 128/419 PG |
| 4,030,510 | 6/1977 | Bowers | 128/419 PG |
| 4,034,347 | 8/1977 | Renirie | 128/419 PG |
| 4,049,003 | 9/1977 | Walters et al. | 128/419 PG |

*Primary Examiner*—William E. Kamm
*Attorney, Agent, or Firm*—Spencer & Kaye

[57] ABSTRACT

A demand pacer has a local memory element, programmable from a remote source, which detects whether or not the hysteresis rate adjustment is to be employed. When hysteresis is disabled, the pacer operates in the normal demand mode, at a rate optionally selected by the same memory. In the hysteresis mode, a flip-flop controls gating means, ultimately operable at conventional or hysteresis rates, ultimately for controlling the output amplifier. An input amplifier senses natural heart beat signals, and enables a gating means, which has been conditioned for hysteresis mode operation, to reset the flip-flop and in turn the output controlling gates.

5 Claims, 3 Drawing Figures

4,169,480

DEMAND PACER WITH PROGRAMMABLE RATE HYSTERESIS

TECHNICAL FIELD

This invention relates to implantable body function control apparatus and particularly, but not exclusively, to body tissue stimulating devices such as cardiac pacemakers.

BACKGROUND ART

Pacemakers for generating artificial stimulating pulses for the heart, and which may be implanted in the body, are well known. Originally the electrical circuitry for such pacemakers was of analog design, but in recent years digital circuitry has been also employed. A digital approach to pacemakers has led to the evolution of programmable pacemakers—pacemakers having parameters such as pulse rates which are adjustable (programmable) once the pacemaker has been implanted. The programs can be changed from outside the patient's body by appropriate signal transmission to the implanted pacemaker and without surgery. Programmable pacemakers are described in, for instance, British Specifications Nos. 1,385,954 and 1,398,875. Such pacemakers have circuitry to detect and decode signals transmitted outside the body and alter the program accordingly. In British Specification No. 1,385,954 (claiming priority based on U.S.S.N. 141,694, in turn a parent of U.S. Pat. No. 3,805,796 to Tenz) the programming is accomplished by means of a magnetic field which is sensed by a magnetic reed switch; the opening and closing of the switch providing programming pulses to a program store. In British Specification No. 1,398,875 (based on U.S. Pat. No. 3,833,005 to Wingrove) the programming is by means of radio frequency transmission and reception.

Many pacemakers are of the demand type—that is they only supply a stimulating pulse to the heart when a natural heart beat is absent. To accomplish this, demand pacemakers have means for sensing the presence or absence of natural heart beats and for actuating the stimulating pulse as appropriate.

It is desirable with a demand pacemaker that the stimulating pulses are issued only when really needed by the heart, and that the latter is given the opportunity of functioning as naturally as possible. One approach to providing this desirable property has been to provide the implanted pacemaker with a fixed hysteresis function for the pacing rate, so that, after each natural heart beat detected which inhibits a stimulating pulse, a slight delay occurs before the next stimulating pulse is generated. Hysteresis is therefore the characteristic of a pacemaker whereby the period of time from a natural heart beat to the next pacing pulse is longer than the period between two successive pacing pulses. This hysteresis, which essentially involves the pacemaker switching over to issuing one stimulating pulse at a slower rate after one or more natural beats has arisen, is of particular use in that it avoids competition between natural heart beats and artificial stimulating pulses, and hence reduces current drain on the pacemaker. It is desirable to allow as many natural beats to arise normally without any stimulation of the heart being provided: by supplying a hysteresis function, a greater opportunity is being given for the natural beats to continue without an artificial pulse being generated.

Not all cardiac specialists agree that a hysteresis function is universally desirable for all pacemakers (see for example, The American Journal of Cardiology, 38, p. 685–688 (1976)), and with currently available pacemekrs this entails a decision on the medical personnel whether or not a pacemaker to be implanted should be one with or without hysteresis in its circuitry. To change this decision entails replacing the implanted pacemaker and hence surgery.

DISCLOSURE OF INVENTION

We have now designed an implantable, demand body tissue stimulating device whereby hysteresis can be included in, or removed from the functioning pacemaker circuitry implanted in the patient's body. The hysteresis function can then be considered as a parameter which is adjustable (programmable) after implant.

According to the invention, we provide an implantable, demand body tissue stimulating apparatus comprising an artificial stimulating pulse generator capable of issuing pulses at at least two pulse rates, means for switching the pulse generator from a first artificial pulse rate to a second artificial pulse rate, slower than the first rate, when an artificial pulse is not demanded by the body and for reverting the pulse generator to the first rate after the issuance of a pulse at the second rate, means for controlling said switching means whereby said switching to the second rate can be inhibited, program store means for controlling said controlling means to determine whether said switching means is to be inhibited, and means for changing the program stored by the program store.

Preferably the body tissue stimulating apparatus is a demand cardiac pacemaker and preferably the program detection means the program store have digital circuitry.

BRIEF DESCRIPTION OF THE DRAWINGS

Preferred features of the invention are illustrated in the accompanying drawings, in which.

BEST MODE FOR CARRYING OUT THE INVENTION

Figure 1:
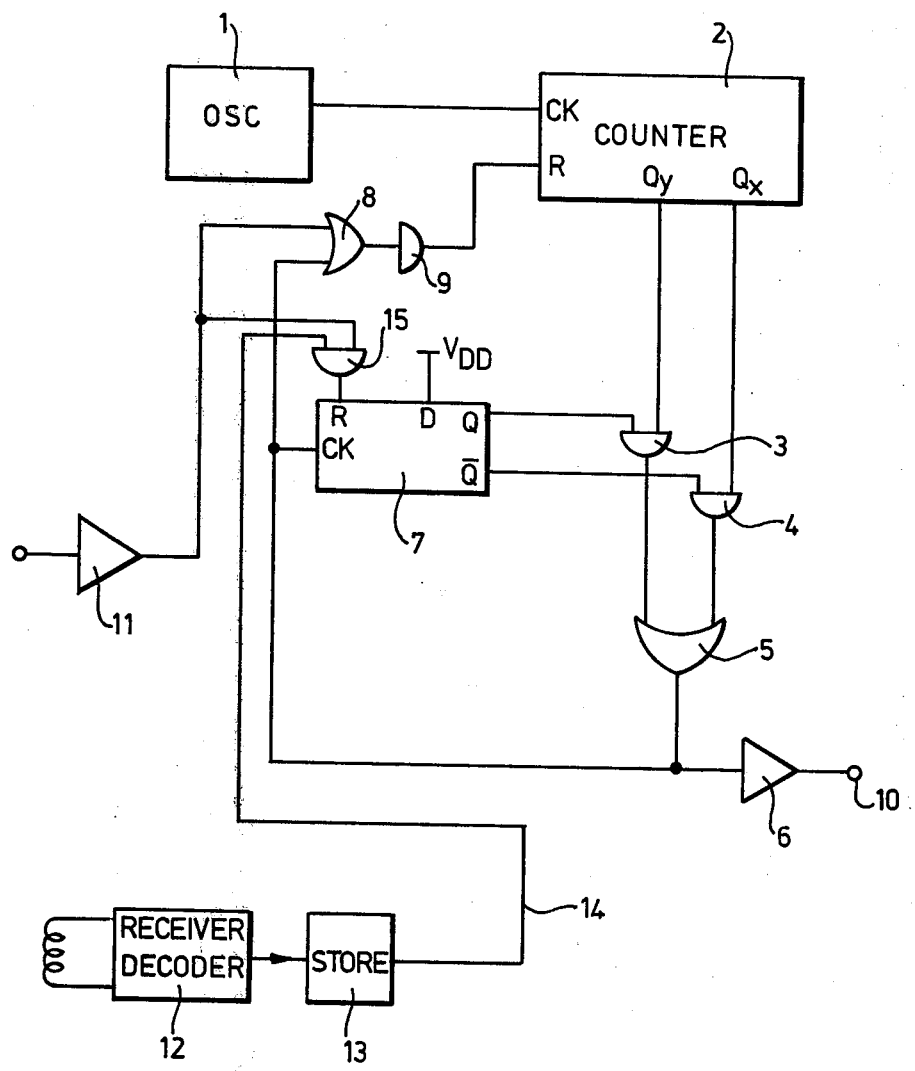
FIG. 1 shows schematically the electrical circuit diagram of an implantable, demand, cardiac pacemaker in which the hysteresis function is programmable.

Referring to FIG. 1, the pacemaker comprises an oscillator 1 which clocks a counter 2. The counter provides two outputs, Qx which can be considered as issuing pulses at a "slow" tissue stimulation pulse rate (e.g. 60 pulses per minute), and Qy which can be considered as issuing pulses at a "normal" tissue stimulation pulse rate (e.g. 70 pulses per minute).

The Qy and Qx outputs supply an input, respectively, to AND gates 3 and 4, whose outputs are provided to an OR gate 5. The output of the latter is supplied to an output amplifier 6, to the clock input of a D-flip-flop 7, and to an OR gate 8. The latter output supplies a delay 9, the output of which is connected to the reset of counter 2.

The output amplifier 6 provides amplified tissue stimulating pulses to a connection 10 for coupling to an electrode leading to the heart.

An input amplifier 11 receives electrical signals detected at the heart (e.g. arising from a natural heart beat) and supplies these to a second input of OR gate 8.

A receiver/decoder 12 is arranged to receive and decode data signals transmitted from outside the patient's body to the implanted pacemaker, and to employ the decoded signals for changing a pacemaker program held in program store 13. For the purposes of illustration, the receiver/decoder 12 and store 13 have been depicted very simply and as providing an output for controlling only the hysteresis function. In practice it would be desirable to make these features much more sophisticated so that the program store is employed to provide a varying control for several different pacemaker parameters (e.g. pulse rate, pulse width, and varying amounts of hysteresis with various programs, depending upon past history of spontaneous beats). The data signals may be transmitted to the receiver/decoder 12 by any suitable means, but preferably we employ data signals transmitted by tone burst modulation (a carrier frequency being pulse width modulated). A receiver/decoder and program store for such data signals is described in our copending Application Ser. No. 917,130 filed on even date (ref. DLD-10). In the illustrated embodiment, the output supplied by program store 13 is a single "bit" of binary information, which is provided on line 14 to an AND gate 15. A second input to AND gate 15 is supplied from input amplifier 11. The output of AND gate 15 is connected to the reset of flip-flop 7. The D-input to flip-flop 7 is supplied from the positive supply rail. The Q and $\overline{Q}$ outputs of flip-flop 7 are supplied as inputs to AND gates 3 and 4, respectively.

The pacemaker functions as follows. Assume initially that the hysteresis function has not been selected. This will be provided by storing a "0" in store 13 so as to prevent any reset for flip-flop 7 via line 14 and AND gate 15 occurring. Assume that, when switched on initially, the counter 2 has issued a count via OR gate 5, and that flip-flop 7 is in the "1" state with its Q output high.

The high Q output of flip-flop 7 enables AND gate 3 and, correspondingly, the low $\overline{Q}$ output disables AND gate 4. In this circumstance, OR gate 5 transmits, to the output amplifier 6, the Qy or "normal" pulse rate provided by counter 2.

In the absence of a natural heart beat being detected and amplified by input amplifier 11, oscillator 1 clocks counter 2 and the Qy "normal" pulses are transmitted to the heart via output amplifier 6 and connection 10. Each issued pulse resets counter 2 via OR gate 8 and delay 9 so that the counter commences its count for the next "normal" pulse. The delay provided by delay 9 sets the pulse width for each pulse issued by counter 2.

If a natural heart beat is detected and amplified by amplifier 11 then this signal resets counter 2 via OR gate 8 and delay 9. This reset, unless it occurs just as counter 2 issues a pulse, prevents counter 2 from generating stimulating pulses and no artificial stimulation is provided to the heart. It is of no consequence if the reset initiated by a natural heart beat, arrives just as an artificial pulse is generated, since the natural beat and the stimulating pulse will essentially coincide.

The circuit thus far described is acting as a conventional demand pacemaker, only issuing tissue stimulating pulses for output to the heart when a natural beat is missing.

Figure 2:
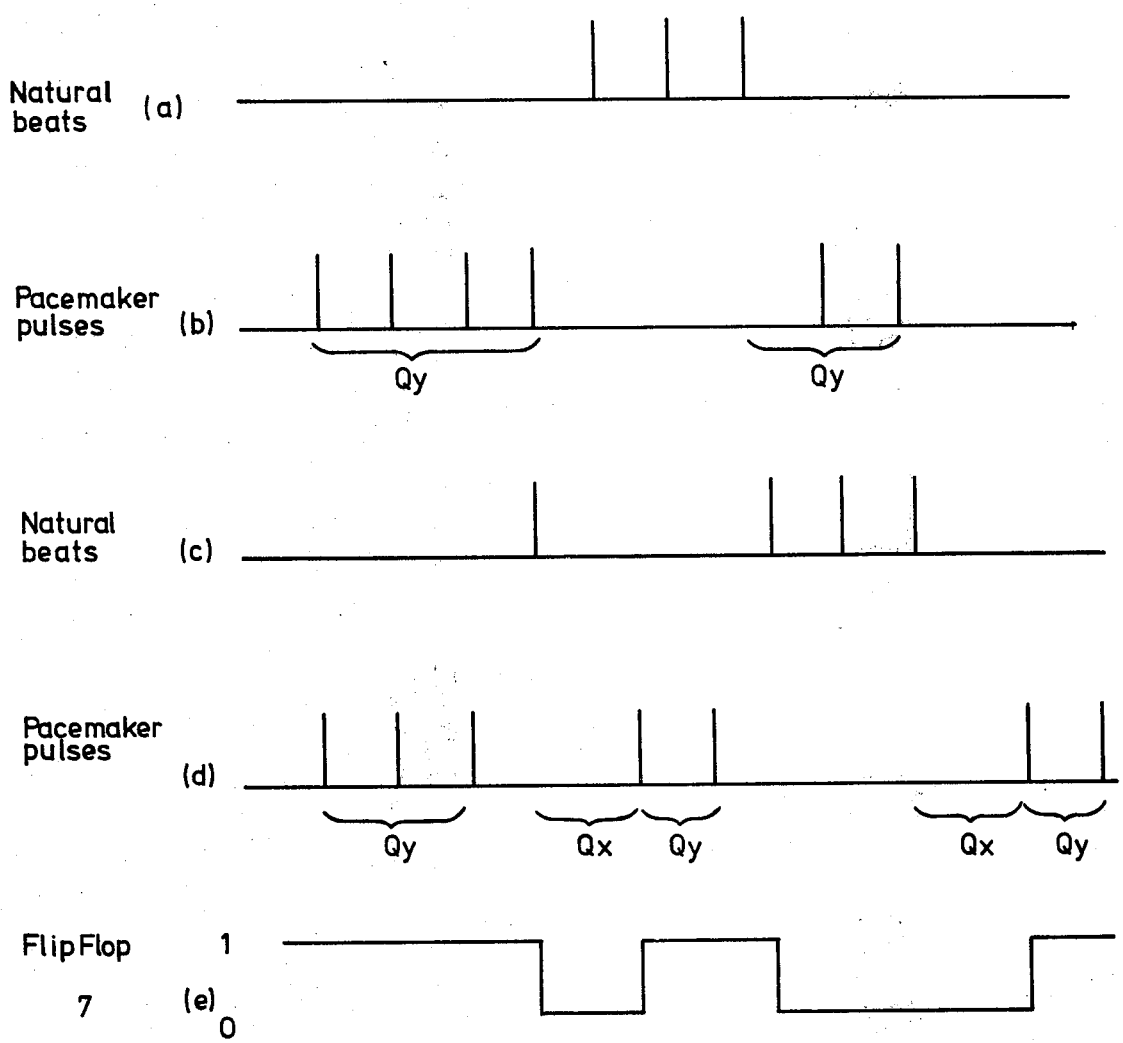
FIG. 2 is an electrical timing diagram for use with FIG. 1.

The pulses received by input amplifier 11 and transmitted, as artificial stimulating pulses, by output amplifier 6 are illustrated in FIG. 2 (a) and (b) respectively.

Assume now that it is desired to select the hysteresis function. In this circumstance a "1" is stored in program store 13 so that a "1" is permanently held on the input line 14 to AND gate 15. In the absence of a natural heart beat, no input is again detected by amplifier 11 and the pacemaker issues "normal" rate tissue stimulating pulses as described above.

If a single natural beat is issued by the heart, this is detected and amplified by amplifier 11 and the signal not only resets counter 2 as described above, but also resets flip-flop 7. The latter thus goes to the "0" state, consequentially disabling AND gate 3 and enabling AND gate 4. This enables the Qx "slow" pulse rate to be steered through OR gate 5 rather than the Qy "normal" rate.

This circumstance causes the next artificial pulse to be issued by counter 2 at a later time than would have been expected at the Qy "normal" rate: it is issued at the Qx "slow" rate. This slight delay provides the hysteresis function for the pacemaker and allows more time for a natural heart beat to be detected and amplified by amplifier 11, so as to inhibit this next artificial pulse. Since we are assuming that only a single natural heart beat arises, no such further natural beat is detected and the Qx "slow" pulse is generated and supplied to the heart. This pulse resets counter 2 via OR gate 8 and delay 9 and also clocks flip-flop 7 so that the latter reverts to the "1" state. This causes a changeover of the states of AND gates 3 and 4 so that there is a reversion to the Qy "normal" pulse rate until the next natural beat resets flip-flop 7 again.

If a succession of natural beats arise, then each will not only reset counter 2 but hold flip-flop 7 reset. The latter holds in the "0" state ready to steer a Qx "slow" pulse to the output once the natural beats decrease in period to below the Qx rate.

The hysteresis function is illustrated by FIG. 2 (c), (d) and (e). With no natural beats arising, artificial pulses are issued at the Qy "normal" rate, but when a natural beat occurs, the next artificial pulse is issued at the Qx "slow" rate. After one "slow" pulse the pacemaker reverts to issuing "normal" pulses until the next natural beat arises. As illustrated the next natural beat is one of a succession of three natural beats and no artificial pulse is issued. At the end of the natural beats, one Qx "slow" pulse is issued before the pacemaker again reverts to its "normal" rate.

As has been mentioned above, in practice program store 13 would have the added capability of altering, inter alia, the "normal" pulse rate. This may be accomplished by expanding the outputs obtained from counter 2, and increasing the number of AND and OR gates 3, 4, and 5, and supplying the outputs of the OR gates to a rate decoder which selects, under control from program store 13, the "normal" rate to be generated.

Figure 3:
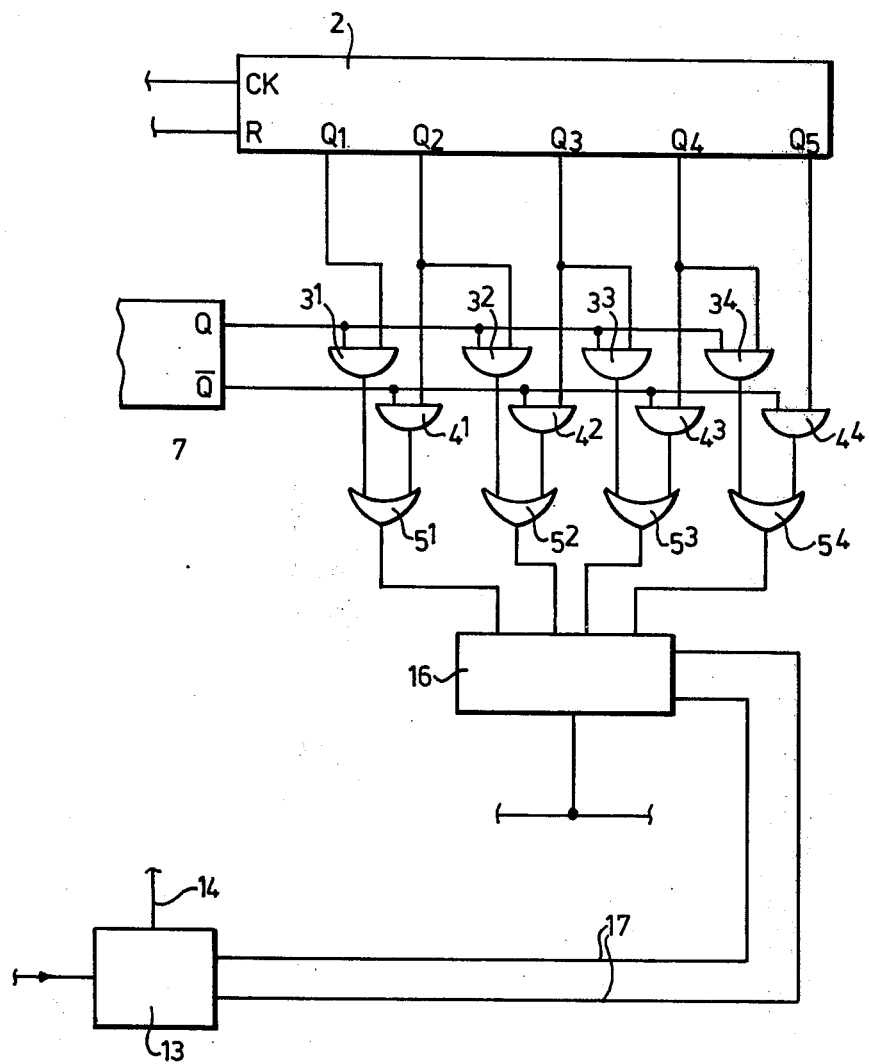
FIG. 3 illustrates an alternative embodiment of the invention which may be employed with FIG. 1.

An example of this is indicated in FIG. 3 where the number of outputs from counter 2 has been expanded to 5 ($Q_1$ to $Q_5$). FIG. 3 is identical to FIG. 1 except as indicated. In FIG. 3, a plurality of AND gates 3 and 4 ($3^1$ to $3^4$, $4^1$ to $4^4$) and OR gates 5 ($5^1$ to $5^4$) exist. For any pair of adjacent outputs from counter 2, the lower numbered stage can be considered as providing the "normal" pulse rate and the adjacent higher numbered stage as providing the "slow" pulse rate (i.e. $Q_1$ normal, $Q_2$ slow; $Q_2$ normal, $Q_3$ slow . . . ). This provides a total of four normal/slow pulse rate combinations which can be individually selected by a rate decoder 16. The particular rate combination selected is determined by the logic levels on lines 17 held in store 13.

What is claimed is:

1. In a programmable pacer system having a remote programming means, an implantable cardiac pacer having remotely programmable rate hysteresis comprising:
    (a) free running timing means having a fixed, predetermined rate;
    (b) counting means, responsive to said timing means, for counting at least to respective first and second count states;
    (c) output amplifier means, for generating artificial stimulating pulses;
    (d) input amplifier means for sensing naturally occurring heartbeat signals;
    (e) switching means, alternatively responsive to said states, for energizing said output amplifier means;
    (f) local memory means, responsive to said remote programming means, for conditioning said pacer system to operate alternatively in conventional demand pacing mode at a rate determined by successive achievement of said first state, or in rate hysteresis mode;
    (g) logic means, energized by said local memory means for said hysteresis mode, and responsive to said input amplifier means, for conditioning said switching means to respond to achievement of said second state upon at least one sensing of a natural heartbeat signal.

2. A pacer as described in claim 1 wherein said switching means comprises a flip-flop having a first logic state to energize said output amplifier in response to said first count state, and a second logic state to energize said output amplifier in response to said second count state.

3. A pacer as described in claim 2 wherein said switching means includes first and second gating means, respectively conditioned by said first and second count states, and being enabled in complementary fashion by said first and second logic states from said flip-flop.

4. A pacer as described in claim 3 wherein said logic means comprises first means responsive alternatively to an artificial stimulating pulse, and to a naturally occurring heartbeat signal, for resetting said counting means to a datum state and for setting said flip-flop to energize said first gating means; and second means, responsive to said memory means for hysteresis mode operation and to a naturally occurring heart-beat signal, for resetting said flip-flop to energize said second gating means.

5. A pacer as described in claim 1 wherein said counting means is adapted for counting to more states than said first and second count states, said more states corresponding to respective predetermined stimulating pulse rates; wherein said memory means further comprises means for selecting one of said more states; and wherein said switching means further includes means, responsive to said memory means, for selecting a given one of said more states for energizing said output amplifier means.

* * * * *